United States Patent [19]

Bitha et al.

[11] Patent Number: 4,665,210
[45] Date of Patent: May 12, 1987

[54] PLATINUM COMPLEXES OF ALIPHATIC TRICARBOXYLIC ACIDS

[75] Inventors: Panayota Bitha, Pomona; Ralph G. Child, Pearl River; Joseph J. Hlavka, Tuxedo; Yang-I Lin, Nanuet, all of N.Y.

[73] Assignee: American Cyanamid Company, Stamford, Conn.

[21] Appl. No.: 790,601

[22] Filed: Oct. 28, 1985

Related U.S. Application Data

[63] Continuation-in-part of Ser. No. 682,951, Dec. 17, 1984, abandoned.

[51] Int. Cl.⁴ ............................................. C07F 15/00
[52] U.S. Cl. .................................. 556/137; 260/414; 514/492
[58] Field of Search ....................... 556/137; 260/414; 514/492

[56] References Cited

U.S. PATENT DOCUMENTS

| | | |
|---|---|---|
| 4,115,418 | 9/1978 | Gale et al. . |
| 4,137,248 | 1/1979 | Gale et al. . |
| 4,140,707 | 2/1979 | Cleare et al. . |
| 4,169,846 | 10/1979 | Kidani et al. . |
| 4,200,583 | 4/1980 | Kidani et al. . |
| 4,255,347 | 3/1981 | Kidani et al. . |
| 4,256,652 | 3/1981 | Kidani et al. . |
| 4,284,579 | 8/1981 | Meischen et al. . |
| 4,359,425 | 11/1982 | Totani et al. . |
| 4,477,387 | 10/1984 | Kidani et al. . |
| 4,533,502 | 8/1985 | Rochon et al. ................. 556/137 X |
| 4,565,884 | 1/1986 | Andrulis, Jr. et al. ............. 556/137 |

FOREIGN PATENT DOCUMENTS 2024823  1/1980  United Kingdom .

Primary Examiner—Helen M. S. Sneed
Attorney, Agent, or Firm—Edward A. Conroy, Jr.; Robert P. Raymond

[57] ABSTRACT

Platinum complexes of aliphatic tricarboxylic acids useful for inducing regression and/or palliation of cancer diseases in mammals.

19 Claims, No Drawings

PLATINUM COMPLEXES OF ALIPHATIC TRICARBOXYLIC ACIDS

CROSS REFERENCE TO RELATED APPLICATION

This application is a continuation-in-part of our co-pending application Ser. No. 682,951, filed Dec. 17, 1984, now abandoned.

SUMMARY OF THE INVENTION

This invention is concerned with new compounds of the formula:

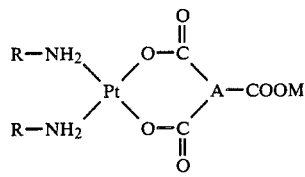

wherein M is cationic hydrogen, sodium or potassium and R is hydrogen or alkyl($C_1$-$C_5$) or when taken together are selected from the group consisting of moieties of the formulae:

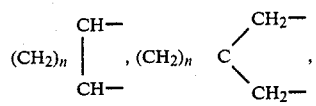

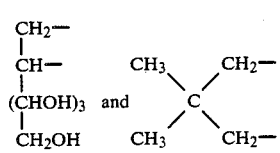

wherein n is the integer 3-5, inclusive; and A is selected from the group consisting of moieties of the formulae:

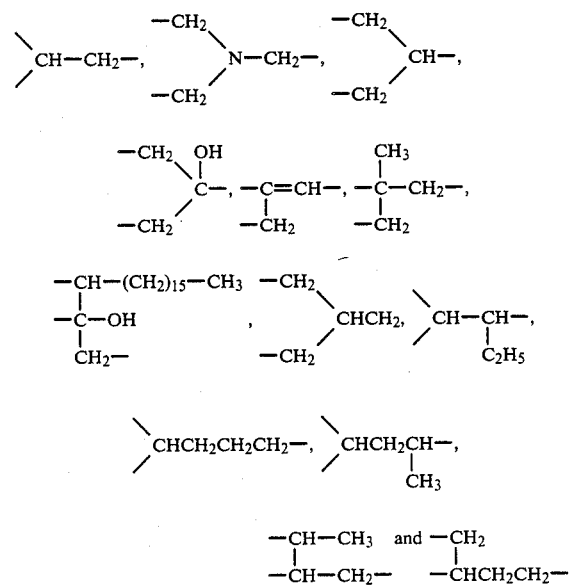

DETAILED DESCRIPTION OF THE INVENTION

The compounds of this invention may be prepared according to the following flowchart.

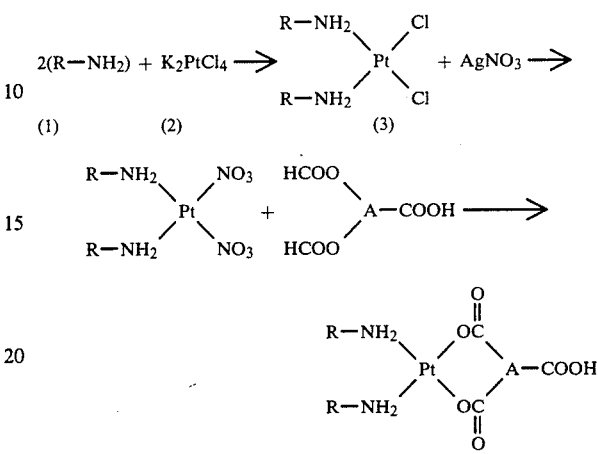

According to the above flowchart, and amine (1) where R is as described above is reacted with potassium tetrachloroplatinate (2) in water giving platinum complex (3) which is then reacted with silver nitrate giving a solution of the platinum nitrate complex (4). The complex (4) is then reacted with a solution of a tricarboxylic acid derivative (5) in the presence of two equilvalents of sodium hydroxide, where A is as described above, in an aqueous base giving the product (6).

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

Lymphocytic Leukemia P388 Test

| Compound | Dose (mg/kg) | Median Survival (Days) | T/C × 100 (%) |
| --- | --- | --- | --- |
| 2,2-dimethyl-1,3-propanedi-amine, compound with [1,1,2-ethanetricarboxylato(2-)-$O^1,O^1$]platinum (1:1) | 100 | 20.5 | 178 |
| | 50 | 20.5 | 178 |
| | 25 | 19.0 | 165 |
| | 12.5 | 16.0 | 139 |
| | 6.2 | 14.5 | 126 |
| Control | — | 11.5 | — |
| Cisplatin | 1 | 29.0 | 252 |
| | 0.25 | 19.0 | 165 |
| | 0.06 | 15.5 | 135 |
| trans-(−)-1,2-cyclohexanedi-amine compound with[1,1,2-ethanetricarboxylato(2-)-$O^1,O^1$]platinum (1:1) | 100 | 22.5 | 214 |
| | 50 | 19.0 | 181 |
| | 25 | 14.0 | 133 |
| | 12 | 15.0 | 143 |
| | 6 | 11.0 | 105 |
| Control | — | 10.5 | — |
| Cisplatin | 1 | 22.0 | 210 |

TABLE I-continued

Lymphocytic Leukemia P388 Test

| Compound | Dose (mg/kg) | Median Survival (Days) | T/C × 100 (%) |
|---|---|---|---|
| | 0.25 | 15.0 | 143 |
| | 0.06 | 13.0 | 124 |
| cis(and trans)-1,2-cyclo-hexanediamine, compound with [[2,2',2''-nitrilotris[acetato]](2-)-O,O¹]platinum (1:1) | 100 | 28.5 | 244 |
| | 50 | 26.0 | 222 |
| | 25 | 24.5 | 209 |
| | 12 | 22.0 | 188 |
| | 6 | 18.5 | 158 |
| Control | — | 11.7 | — |
| Cisplatin | 1 | 27.0 | 231 |
| | 0.25 | 17.5 | 150 |
| | 0.06 | 15.0 | 128 |
| trans-(−)-1,2-cyclohexanediamine compound with [[2,2',2''-nitrilotris[acetato]](2-)O,O¹]platinum (1:1) | 100 | 25 | 214 |
| | 50 | 24 | 205 |
| | 25 | 19 | 162 |
| | 12 | 20 | 171 |
| | 6 | 16 | 137 |
| Control | — | 11.7 | — |
| Cisplatin | 1 | 27 | 231 |
| | 0.25 | 17.5 | 150 |
| | 0.06 | 15 | 128 |
| cis(and trans)-1,2-cyclohexanediamine, compound with [2-hydroxy-1,2,3-propanetricarboxylato(2-)-O¹,O³]platinum (1:1) | 50 | 22 | 188 |
| | 25 | 21 | 179 |
| | 12 | 20 | 171 |
| | 6 | 15 | 128 |
| Control | — | 11.7 | — |
| Cisplatin | 1.0 | 27 | 231 |
| | 0.25 | 17.5 | 150 |
| | 0.06 | 15 | 128 |
| cis(and trans)-1,2-cyclohexanediamine, compound with [1,2,3-propanetricarboxylato(2-)-O¹,O³]platinum (1:1) | 50 | 24.5 | 223 |
| | 25 | 26 | 236 |
| | 12 | 24 | 218 |
| | 6 | 19 | 173 |
| Control | — | 11 | — |
| Cisplatin | 1 | 27.5 | 250 |
| | 0.25 | 19.5 | 177 |
| | 0.06 | 15 | 136 |
| 1,1-cyclobutanedimethanamine, compound with [1,1,2-ethanetricarboxylato (2-)-O¹,O¹]platinum (1:1) | 100 | 19.5 | 193 |
| | 50 | 17.5 | 173 |
| | 25 | 15.5 | 153 |
| | 12 | 14.5 | 144 |
| | 6 | 12.5 | 124 |
| | 3 | 12.5 | 124 |
| Control | — | 10.1 | — |
| Cisplatin | 1 | 23 | 228 |
| | 0.25 | 19 | 188 |
| | 0.06 | 16.5 | 163 |
| | 0.015 | 13.5 | 134 |
| cis(and trans)-1,2-cyclohexanediamine, compound with [1,1,2-ethanetricarboxylato-(2-)-O¹,O¹]platinum (1:1) | 50 | 18 | 178 |
| | 25 | 14 | 139 |
| | 12 | 14.5 | 144 |
| | 6 | 12 | 119 |
| | 3 | 15 | 149 |
| | 1.5 | 12.5 | 124 |
| Control | — | 10.1 | — |
| Cisplatin | 1 | 23 | 228 |
| | 0.25 | 19 | 188 |
| | 0.06 | 16.5 | 163 |
| | 0.015 | 13.5 | 134 |
| (1S-trans)-(−)-1,2-cyclohexaneamine, compound with [2-hydroxy-1,2,3-propanetricarboxylato-(2-)-O¹,O³]platinum (1:1) | 100 | 19 | 188 |
| | 50 | 19 | 188 |
| | 25 | 18.5 | 183 |
| | 12 | 16 | 158 |
| | 6 | 14.5 | 144 |
| | 3 | 12 | 119 |
| Control | — | 10.1 | — |
| Cisplatin | 1 | 23 | 228 |
| | 0.25 | 19 | 188 |
| | 0.06 | 16.5 | 163 |
| | 0.015 | 13.5 | 134 |
| 1,2-diamino-1,2-dideoxy-D-glucitol, compound with [1,1,2-ethanetricarboxylato-(2-)-O¹,O¹]platinum (1:1) | 100 | 17.2 | 124 |
| | 50 | 16.5 | 119 |
| | 25 | 16.5 | 119 |
| | 12 | 15 | 109 |
| | 6 | 15 | 109 |
| Control | — | 13.8 | — |
| Cisplatin | 1 | 23.5 | 170 |
| | 0.25 | 22.0 | 159 |
| | 0.06 | 20 | 145 |
| | 0.015 | 20 | 145 |
| trans-(−)-1,2-cyclohexanediamine, compound with [2-hydroxy-1,2,3-nonadecanetricarboxylato(2-)O²,O³]platinum (1:1) | 100 | 14.5 | 132 |
| | 50 | 18.5 | 168 |
| | 25 | 12 | 109 |
| | 12 | 12.5 | 114 |
| Control | — | 11 | — |
| Cisplatin | 1 | 24 | 214 |
| | 0.25 | 15.5 | 141 |
| | 0.06 | 13 | 118 |
| | 0.015 | 12 | 109 |
| trans(1,2-cyclohexanediamine-N—N')[1,1,2-ethanetricarboxylato(3-)O¹,O¹]platinate (1-), sodium salt | 50 | 25 | 227 |
| | 25 | 22.5 | 205 |
| | 12.5 | 20 | 182 |
| | 6.2 | 18.5 | 168 |
| | 3.1 | 14.5 | 132 |
| Control | — | 11 | — |
| Cisplatin | 2 | 15.5 | 141 |
| | 1 | 26.5 | 241 |
| (2,2-dimethyl-1,3-propanediamine-N,N')[1,1,2-ethanetricarboxylato(3-)-O¹,O¹]platinate(1-), sodium salt | 100 | 17 | 170 |
| | 50 | 20 | 200 |
| | 25 | 16 | 160 |
| | 12.5 | 16 | 160 |
| | 6.2 | 12.5 | 125 |
| | 3.1 | 13 | 130 |
| Control | — | 10 | — |
| Cisplatin | 2 | 10.5 | 105 |
| | 1 | 23.5 | 235 |

Melanotic Melanoma B16

The animals used were C57BC/6 mice, all of the same sex, weighing a minimum of 17 g and all within a 3 g weight range. There were 10 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test on representative compounds of this invention appear in Table II.

TABLE II

Melanotic Melanoma B₁₆ Test

| Compound | Dose (mg/kg) | Median Survival (Days) | T/C × 100 (%) |
|---|---|---|---|
| 2,2-dimethyl-1,3-propanediamine, compound with [1,1,2-ethanetricarboxylato(2-)-O¹,O¹]platinum (1:1) | 100 | 25 | 170 |
| | 50 | 22.5 | 153 |
| | 25 | 20.5 | 139 |
| | 12.5 | 19.5 | 133 |
| | 6.25 | 17.5 | 119 |
| Control | — | 14.7 | — |
| Cisplatin | 0.4 | 18.5 | 126 |
| | 0.2 | 21 | 143 |
| | 0.1 | 18 | 122 |
| | 0.05 | 19 | 129 |
| trans-(−)-1,2-cyclohexanediamine, compound with [1,1,2-ethanetricarboxylato(2-)-O¹,O¹]platinum (1:1) | 25 | 28 | 175 |
| | 12 | 26.5 | 166 |
| | 6 | 23.5 | 147 |
| | 3 | 22.5 | 141 |
| | 1.5 | 20.1 | 126 |
| Control | — | 16 | — |
| Cisplatin | 0.4 | 25 | 156 |

TABLE II-continued

Melanotic Melanoma B16 Test

| Compound | Dose (mg/kg) | Median Survival (Days) | T/C × 100 (%) |
|---|---|---|---|
| | 0.2 | 25 | 156 |
| | 0.1 | 23 | 144 |
| | 0.05 | 21.5 | 134 |
| cis(and trans)-1,2-cyclo-hexanediamine, compound with [[2,2',2''-nitrilotris[ace-tato]](2-)-O,O']platinum (1:1) | 25 | 29.5 | 180 |
| | 12 | 28 | 171 |
| | 6 | 24.5 | 149 |
| | 3 | 25 | 152 |
| | 1.5 | 21 | 128 |
| Control | — | 16.4 | — |
| Cisplatin | 1.4 | 26.5 | 162 |
| | 0.2 | 23 | 140 |
| | 0.1 | 21 | 128 |
| | 0.05 | 21 | 128 |
| trans-(−)-1,2-cyclohexane-diamine, compound with [[2,2',2''-nitrilotris[ace-tato]](2-)-O,O']platinum (1:1) | 25 | 27 | 169 |
| | 12 | 26.5 | 166 |
| | 6 | 27 | 169 |
| | 3 | 26.5 | 166 |
| | 1.5 | 20 | 125 |
| Control | — | 16 | — |
| Cisplatin | 0.4 | 25 | 156 |
| | 0.2 | 25 | 156 |
| | 0.1 | 23 | 144 |
| | 0.05 | 21.5 | 134 |
| cis(and trans)-1,2-cyclo-hexanediamine, compound with [1,2,3-propanetricarboxylato-(2-)-O¹,O³]platinum (1:1) | 12 | 31.5 | 192 |
| | 6 | 28 | 171 |
| | 3 | 25 | 152 |
| | 1.5 | 22.5 | 137 |
| Control | — | 16.4 | — |
| Cisplatin | 0.4 | 26.5 | 162 |
| | 0.2 | 23 | 140 |
| | 0.1 | 21 | 128 |
| | 0.05 | 21 | 128 |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implat was by intraperitoneal or subcutaneous injection of 0.5 ml of a 2% Colon 26 tumor brei in Eagle's MEM medium containing antibiotics. The test compounds were administered intraperitoneally on days 1, 5 and 9 (relative to tumor implant at various doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

Colon 26 Adenocarcinoma Test

| Compound | Dose (mg/kg) | Median Survival (Days) | T/C × 100 (%) |
|---|---|---|---|
| trans-(−)-1,2-cyclohexanedi-amine, compound with [1,1,2-ethanetricarboxylato(2-)-O¹,O¹]platinum (1:1) | 50 | 18.5 | 112 |
| | 25 | 22 | 133 |
| Control | — | 16.5 | — |
| Cisplatin | 1 | 18.5 | 112 |
| | 0.5 | 30.5 | 185 |
| | 0.25 | 29.5 | 179 |
| cis(and trans)-1,2-cyclo-hexanediamine, compound with [[2,2',2''-nitrilotris[ace-tato]](2-)-O,O']platinum (1:1) | 100 | 30.5 | 185 |
| | 50 | 20.5 | 124 |
| | 25 | 22.5 | 136 |
| Control | — | 16.5 | — |

TABLE III-continued

Colon 26 Adenocarcinoma Test

| Compound | Dose (mg/kg) | Median Survival (Days) | T/C × 100 (%) |
|---|---|---|---|
| Cisplatin | 1 | 18.5 | 112 |
| | 0.5 | 30.5 | 185 |
| | 0.25 | 29.5 | 179 |
| trans-(−)-1,2-cyclohexane-diamine, compound with [[2,2',2''-nitrilotris[ace-tato]](2-)-O,O']platinum (1:1) | 50 | 18.5 | 112 |
| | 25 | 18.5 | 112 |
| | 12 | 18 | 109 |
| Control | — | 16.5 | — |
| Cisplatin | 1 | 18.5 | 112 |
| | 0.5 | 30.5 | 185 |
| | 0.25 | 29.5 | 179 |
| cis(and trans)-1,2-cyclo-hexanediamine, compound with [1,2,3-propanetricarboxylato-(2-)-O¹,O³]platinum (1:1) | 25 | 21.5 | 130 |
| | 12 | 24 | 145 |
| Control | — | 16.5 | — |
| Cisplatin | 1 | 18.5 | 112 |
| | 0.5 | 30.5 | 185 |
| | 0.25 | 29.5 | 179 |

Lymphocytic Leukemia L1210 Test

The animals used were BDF₁ or CD₂F₁ mice, all of one sex, weighing a minimum of 17 g and all within a 3 g weight range. There were 6 mice in each test group and 18 mice in control groups. The tumor transplant was by intraperitoneal injection of 0.5 ml of lymphocytic leukemia L1210 at a concentration of 10⁵ cells per mouse. The test compounds were administered on days 1, 5 and 9 relative to tumor inoculation at various doses. The mice were weighed and survivors recorded on a regular basis for 30 days. The median survival time and the ratio of survival time for treated (T)/control (C) mice were calculated. The positive control compounds were Cisplatin and 5-Fluorouracil given intraperitoneally at the indicated doses. The results of this test on representative compounds of this invention appear in Table IV.

TABLE IV

Lymphocytic Leukemia L1210 Test

| Compound | Dose (mg/kg) | Median Survival (Days) | T/C × 100 (%) |
|---|---|---|---|
| 2,2-dimethyl-1,3-propanedi-amine, compound with [1,1,2-ethanetricarboxylato (2-)-O¹,O¹]platinum (1:1) | 100 | 12.4 | 151 |
| | 50 | 27.2 | 332 |
| | 25 | 27.0 | 329 |
| | 12.5 | 12.2 | 149 |
| Control | — | 8.2 | — |
| Cisplatin | 6 | 12.2 | 149 |
| | 3 | 16.6 | 202 |
| | 1.5 | 11.8 | 144 |
| 5-Fluoruracil | 60 | 20.2 | 246 |
| trans-(−)-1,2-cyclohexane-diamine, compound with [1,1,2-ethane tricarboxylato (2-)-O¹,O¹]platinum (1:1) | 100 | 13.6 | 132 |
| | 50 | 21.0 | 204 |
| | 25 | 25.8 | 250 |
| | 12.5 | 15.2 | 148 |
| Control | — | 10.3 | — |
| Cisplatin | 6 | 20.8 | 202 |
| | 3 | 14.2 | 138 |
| | 1.5 | 13.4 | 130 |
| 5-Fluoruracil | 60 | 14.8 | 144 |
| cis(and trans)-1,2-cyclo-hexanediamine, compound with [[2,2',2''-nitrilotris[ace-tato]](2-)-O,O']platinum (1:1) | 100 | 24.2 | 235 |
| | 50 | 18.4 | 179 |
| | 25 | 14.6 | 142 |
| | 12.5 | 13.0 | 126 |
| Control | — | 10.3 | — |
| Cisplatin | 6 | 20.8 | 202 |
| | 3 | 14.2 | 138 |
| | 1.5 | 13.4 | 130 |

TABLE IV-continued

Lymphocytic Leukemia L1210 Test

| Compound | Dose (mg/kg) | Median Survival (Days) | T/C × 100 (%) |
|---|---|---|---|
| 5-Fluorouracil | 60 | 14.8 | 144 |
| trans-(−)-1,2-cyclohexane- | 100 | 23.8 | 231 |
| compound with [[2,2′,2″- | 50 | 18.6 | 181 |
| nitrilotris[acetato]](2-)- | 25 | 14.8 | 144 |
| O,O′]platinum (1:1) | 12.5 | 12.2 | 118 |
| Control | — | 10.3 | — |
| Cisplatin | 6 | 20.8 | 202 |
|  | 3 | 14.2 | 138 |
|  | 1.5 | 13.4 | 130 |
| 5-Fluorouracil | 60 | 14.8 | 144 |
| cis(and trans)-1,2-cyclo- | 12.5 | 27.0 | 262 |
| hexanediamine, compound with | 10 | 24.8 | 241 |
| [2-hydroxy-1,2,3-propanetri- | 5 | 18.0 | 175 |
| carboxylato(2-)-O$^1$,O$^3$]- | 2.5 | 12.6 | 122 |
| platinum (1:1) |  |  |  |
| Control | — | 10.3 | — |
| Cisplatin | 6 | 20.8 | 202 |
|  | 3 | 14.2 | 138 |
|  | 1.5 | 13.4 | 130 |
| 5-Fluorouracil | 60 | 14.8 | 144 |
| cis(and trans)-1,2-cyclo- | 50 | 20.4 | 243 |
| hexanediamine, compound with | 25 | 24.8 | 295 |
| [1,2,3-propanetricarboxylato- | 12.5 | 14.4 | 171 |
| (2-)-O$^1$,O$^3$]platinum (1:1) |  |  |  |
| Control | — | 8.4 | — |
| Cisplatin | 6 | 16.0 | 190 |
|  | 3 | 12.2 | 145 |
|  | 1.5 | 10.0 | 119 |
| 5-Fluorouracil | 60 | 14.4 | 171 |
| 1,1-cyclobutanedimethanamine, | 50 | 23.2 | 252 |
| compound with [1,1,2-ethane- | 25 | 22.4 | 243 |
| tricarboxylato (2-)-O$^1$,O$^1$]- | 12.5 | 13.0 | 141 |
| platinum (1:1) |  |  |  |
| Control | — | 9.2 | — |
| Cisplatin | 6 | 16.0 | 174 |
|  | 3 | 12.0 | 130 |
|  | 1.5 | 11.0 | 120 |
| 5-Fluorouracil | 60 | 15.4 | 167 |
| cis(and trans)-1,2-cyclo- | 50 | 15.0 | 179 |
| hexanediamine, compound with | 25 | 21.8 | 260 |
| [1,1,2-ethanetricarboxylato- | 12.5 | 14.8 | 176 |
| (2-)-O$^1$,O$^1$]platinum (1:1) |  |  |  |
| Control | — | 8.4 | — |
| Cisplatin | 6 | 16.0 | 190 |
|  | 3 | 12.2 | 145 |
|  | 1.5 | 10.0 | 119 |
| 5-Fluorouracil | 60 | 14.4 | 171 |

Cisplatin Resistant Lymphocytic Leukemia L1210/Cis DPP

The L1210/Cis DPP tumor is a subline of L1210 leukemia, resistant to Cisplatin and maintained as an ascites tumor in DBA/2 mice. The assay for antitumor activity was performed as described above for L1210. The results on representative compounds of this invention appear in Table V.

TABLE V

Ciplatin Restant Lymphocytic Leukemia L1210/Cis DPP Test

| Compound | Dose (mg/kg) | Median Survival (Days) | T/C × 100 (%) |
|---|---|---|---|
| 2,2-dimethyl-1,3-propanedi- | 100 | 15.2 | 197 |
| amine, compound with [1,1,2- | 50 | 26.8 | 348 |
| ethanetricarboxylato (2-)- | 25 | 8.8 | 114 |
| O$^1$,O$^1$]platinum (1:1) | 12.5 | 8.0 | 104 |
| Control | — | 7.7 | — |
| Cisplatin | 6 | 8.8 | 114 |
|  | 3 | 8.0 | 104 |
|  | 1.5 | 8.6 | 112 |
| 5-Fluorouracil | 60 | 30 | 390 |
| trans-(−)-1,2-cyclohexane- | 100 | 21.8 | 256 |
| diamine, compound with [1,1,2- | 50 | 22.6 | 266 |
| ethanetricarboxylato (2-)- | 25 | 22.8 | 268 |
| O$^1$,O$^1$]platinum (1:1) | 12.5 | 17.8 | 209 |
| Control | — | 8.5 | — |
| Cisplatin | 6 | 9.2 | 108 |
|  | 3 | 9.2 | 108 |
|  | 1.5 | 9.4 | 111 |
| 5-Fluorouracil | 60 | 27.2 | 320 |
| cis(and trans)-1,2-cyclo- | 100 | 20.8 | 245 |
| hexanediamine, compound with | 50 | 26.0 | 306 |
| [[2,2′,2″-nitrilotris[ace- | 25 | 14.4 | 169 |
| tato]](2-)-O,O′]platinum | 12.5 | 10.4 | 122 |
| (1:1) |  |  |  |
| Control | — | 8.5 | — |
| Cisplatin | 6 | 9.2 | 108 |
|  | 3 | 9.2 | 108 |
|  | 1.5 | 9.4 | 111 |
| 5-Fluorouracil | 60 | 27.2 | 320 |
| trans-(−)-1,2-cyclohexane- | 100 | 26.4 | 311 |
| diamine, compound with | 50 | 26.2 | 308 |
| [[2,2′2,2″-nitrilotris[ace- | 25 | 14.2 | 167 |
| tato]](2-)-O,O$^1$]platinum | 12.5 | 10.6 | 125 |
| (1:1) |  |  |  |
| Control | — | 8.5 | — |
| Cisplatin | 6 | 9.2 | 108 |
|  | 3 | 9.2 | 108 |
|  | 1.5 | 9.4 | 111 |
| 5-Fluorouracil | 60 | 27.2 | 320 |
| cis(and trans)-1,2-cyclo- | 12.5 | 30.0 | 353 |
| hexanediamine, compound with | 10 | 20.6 | 242 |
| [2-hydroxy-1,2,3-propanetri- | 5 | 11.4 | 134 |
| carboxylato(2-)-O$^1$,O$^3$]- | 2.5 | 10.2 | 120 |
| platinum (1:1) |  |  |  |
| Control | — | 8.5 | — |
| Cisplatin | 6 | 9.2 | 108 |
|  | 3 | 9.2 | 108 |
|  | 1.5 | 9.4 | 111 |
| 5-Fluorouracil | 60 | 27.2 | 320 |
| cis(and trans)-1,2-cyclo- | 50 | 30.0 | 361 |
| hexanediamine, compound with | 25 | 22.8 | 275 |
| [1,2,3-propanetricarboxylato- | 12.5 | 12.0 | 145 |
| (2-)-O$^1$,O$^3$]platinum (1:1) |  |  |  |
| Control | — | 8.3 | — |
| Cisplatin | 6 | 8.2 | 99 |
|  | 3 | 8.4 | 101 |
|  | 1.5 | 8.2 | 99 |
| 5-Fluorouracil | 60 | 19.2 | 231 |
| 1,1-cyclobutanedimethanamine, | 100 | 11.2 | 127 |
| compound with [1,1,2-ethane- | 50 | 17.0 | 193 |
| tricarboxylato (2-)-O$^1$,O$^1$]- | 25 | 10.2 | 116 |
| platinum (1:1) | 12.5 | 10.0 | 114 |
| Control | — | 8.8 | — |
| Cisplatin | 6 | 8.0 | 91 |
|  | 3 | 9.6 | 109 |
|  | 1.5 | 8.6 | 98 |
| cis(and trans)-1,2-cyclo- | 50 | 17.8 | 214 |
| hexanediamine, compound with | 25 | 26.0 | 313 |
| [1,1,2-ethanetricarboxylato- | 12.5 | 21.4 | 258 |
| (2-)-O$^1$,O$^1$]platinum (1:1) |  |  |  |
| Control | — | 8.3 | — |
| Cisplatin | 6 | 8.2 | 99 |
|  | 3 | 8.4 | 101 |
|  | 1.5 | 8.2 | 99 |
| 5-Fluorouracil | 60 | 19.2 | 231 |

M5076 Sarcoma

The M5076 reticular cell Sarcoma is propagated as subcutaneous (sc) implants in C57B2/6 female mice. In the assays for antitumor activity, BDF$_1$ mice of either sex were inoculated sc with 0.5 ml of a 10% tumor brei. Test compounds were administered ip on days 1, 5, 9, 13 and 17 relative to tumor inoculation on day zero.

Tumor measurements in mm were made by means of a vernier caliper on day 22 relative to tumor implantation and tumor weights in mg estimated by the formula:

$$\frac{\text{length} \times (\text{width})^2}{2}$$

with appropriate T/C values being calculated. The results of this test on representative compounds of this invention appear in Table VI, compared to the results obtained with Cisplatin and Cytoxan.

TABLE VI

M5076 Sarcoma

| Compound | Dose (mg/kg) | Av. Tumor Wt. (mg) | T/C × 100 (%) |
|---|---|---|---|
| 2,2-dimethyl-1,3-propanedi- | 50 | 0 | 0 |
| amine, compound with [1,1,2- | 25 | 0 | 0 |
| ethanetricarboxylato (2-)- | 12.5 | 47 | 2 |
| O¹,O¹]platinum (1:1) | 6.2 | 736 | 38 |
| Control | — | 1927 | — |
| Cisplatin | 6.0 | 0 | 0 |
|  | 3.0 | 361 | 19 |
|  | 1.5 | 865 | 45 |
| trans-(−)-1,2-cyclohexane- | 50 | 0 | 0 |
| diamine, compound with | 25 | 0 | 0 |
| [1,1,2-ethanetricarboxylato | 12.5 | 0 | 0 |
| (2-)-O¹,O¹]platinum (1:1) | 6.2 | 103 | 5 |
| Control | — | 1927 | — |
| Cisplatin | 6.0 | 0 | 0 |
|  | 3.0 | 361 | 91 |
|  | 1.5 | 865 | 45 |
| cis(and trans)-1,2-cyclo- | 50 | 0 | 0 |
| hexanediamine, compound with | 25 | 109 | 6 |
| [[2,2',2"-nitrilotris[ace- | 12.5 | 555 | 29 |
| tato]](2-)-O,O']platinum (1:1) | 6.2 | 1032 | 54 |
| Control | — | 1927 | — |
| Cisplatin | 6 | 0 | 0 |
|  | 3 | 361 | 19 |
|  | 1.5 | 865 | 45 |
| cis(and trans)-1,2-cyclo- | 12.5 | 0 | 0 |
| hexanediamine, compound with | 6.2 | 0 | 0 |
| [2-hydroxy-1,2,3-propanetri- | 3.1 | 38 | 3 |
| carboxylato(2-)-O¹,O³]- |  |  |  |
| platinum (1:1) |  |  |  |
| Control | — | 1174 | — |
| Cisplatin | 6.0 | 0 | 0 |
|  | 3.0 | 149 | 13 |
|  | 1.5 | 0 | 0 |

Human Breast (MX-1) Tumor Xenograft

The human breast (MX-1) carcinoma is propagated as subcutaneous (sc) implants in athymic (Balb/c nude) mice. In assays for antitumor activity, athymic (Balb/c nude) male mice were implanted sc with four to five 2 mm² tumor fragments on day zero. Test compounds were administered intraperitoneally (ip) once every fourth day for a total of three injections starting when tumors were approximately 100 mg in size (staging day, usually 14 days after tumor implantation). Tumor measurements were made in mm by means of a Vernier caliper on days 12 and 16 relative to staging day and tumor weights in mg estimated from the formula $$\frac{\text{Length} \times (\text{width})^2}{2}.$$

The difference ( ) in mean tumor weight (mean final tumor weight minus mean initial tumor weight) was determined for each test group and the treated (T)/control (C) value expressed in percent. The results of this test on a representative compound of this invention appears in Table VII. The positive control compound was Cisplatin.

TABLE VII

Human Breast (MX-1) Tumor Xenograft

| | | Days Post Staging | | | | | |
|---|---|---|---|---|---|---|---|
| | | 12 | | | 16 | | |
| Compound | Dose (mg/kg) | Δ Tumor Wt (mg) | T/C × 100 (%) | Survivors Treated | Δ Tumor Wt (mg) | T/C × 100 (%) | Survivors Treated |
| 2,2-dimethyl-1,3- propanediamine, compound with [1,1,2-ethane- tricarboxylato(2)- O¹,O¹]platinum (1:1) | 50 | −71 | −56 | ¾ | | | 0/4 |
| | 25 | −05 | −06 | ¾ | | | 0/4 |
| | 12.5 | 68 | 12 | ¾ | 100 | 12 | ¾ |
| Control | — | 549 | — | 8/8 | 814 | — | 8/8 |
| Cisplatin | 80 | −31 | −54 | 5/5 | −43 | −75 | 5/5 |

This aspect of the invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use the preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjunction with the following non-limiting specific examples.

EXAMPLE 1

2,2-Dimethyl-1,3-propanediamine, compound with [1,1,2-ethanetricarloxylato(2-)-$O^1,O^1$]platinum (1:1)

To a solution of 12.45 g of potassium tetrachloroplatinate in 60 ml of water was added 3.06 g of 2,2-dimethyl-1,3-propanediamine. This mixture was allowed to stand overnight and then the solid was collected, giving 7.0 g of 2,2-dimethyl-1,3-propanediamine compound with platinum chloride (1:1).

A reaction mixture comprising 49.2 g of triethyl 1,1,2-ethanetricarboxylate, 135 ml of 5N sodium hydroxide and 65 ml of water was stirred at 100° C. for 3 hours, then cooled and concentrated to about 150 ml. A 50 ml portion of cold concentrated hydrochloric acid was added and the mixture was extracted three times with ether. The ether extracts were combined, dried and evaporated, giving 12.5 g of 1,1,2-ethanetricarboxylic acid, mp 169°–170° C.

To a suspension of 3.68 g of 2,2-dimethyl-1,3-propanediamine compound with platinum chloride (1:1) in 30 ml of water was added a solution of 3.40 g silver nitrate in 30 ml of water. This mixture was stirred in the dark for 3 hours and then filtered. To the filtrate was added a solution of 1.62 g of 1,1,2-ethanetricarboxylic acid in 20 ml of 1N sodium hydroxide. This mixture was allowed to stand for 3 hours and then filtered. The filtrate was concentrated almost to dryness and then refrigerated. The resulting solid was collected, washed with water and dried, giving 2.3 g of the desired product as a colorless solid.

EXAMPLE 2 trans-(−)-1,2-Cyclohexanediamine, compound with [1,1,2-ethanetricarboxylato(2)-$O^1,O^1$]platinum (1:1)

A 4.56 g portion of trans-1,2-diaminocyclohexane was dissolved in 20 ml of water. To this solution was added a solution of 16.6 g of potassium tetrachloroplatinate in 100 ml of water. After standing 2.5 hours the solid was collected, washed with water and dried, giving 12.98 g of trans-(−)-1,2-cyclohexanediamine, compound with platinum chloride (1:1).

A 2 g portion of trans-(−)-1,2-cyclohexanediamine, compound with platinum chloride (1:1) was suspended in 20 ml of water and a solution of 1.8 g of silver nitrate in 20 ml of water was added. The suspension was stirred for 3 hours and then filtered. The filtrate was added to a solution of 859 mg of 1,1,2-ethanetricarboxylic acid in 5.3 ml of 2M potassium hydroxide, stirred for 2.5 hours and then evaporated to dryness. The residue was slurried in 5 ml of water. The solid was collected, washed with cold water and dried, giving 868 mg of the desired product.

EXAMPLE 3 cis(and trans)-1,2-Cyclohexanediamine, compound with [[2,2'2''-nitrilotris[acetato]](2-)-O,O']platinum (1:1)

To a solution of 4.56 g of 1,2-diaminocyclo-hexane in 20 ml of water was added a solution of 16.6 g of potassium tetrachloroplatinate in 100 ml of water. The resulting suspension was stirred overnight and the solid recovered, washed with water and dried, giving 15 g of 1,2-cyclohexanediamine, compound with platinum chloride (1:1).

A 5.73 g portion of nitrilotriacetic acid was slurried in 40 ml of water and 6 ml of 10N sodium hydroxide was added. To the resulting solution was added a solution of 10.19 g of silver nitrate in 20 ml of water. This suspension was stirred in the dark overnight and the solid collected, washed with water and dried, giving 11.6 g of 2,2',2''-nitrilotris-acetic acid, disilver salt as a white solid.

A 1.14 g portion of 1,2-cyclohexanediamine, compound with platinum chloride (1:1) was slurried in 100 ml of water. To the resulting suspension was added 1.21 g of 2,2',2''-nitrilotris-acetic acid, disilver salt. The suspension was stirred in the dark overnight and then filtered. The filtrate was evaporated to dryness and the residue slurried in methanol and diluted with ether. The resulting solid was collected and dried, giving 1.39 g of the desired product as a white solid.

EXAMPLE 4 trans-(−)-1,2-Cyclohexanediamine, compound with [[2,2',2''-nitrilotris[acetato]](2-)-O,O']platinum (1:1)

A suspension of 1.14 g of trans-(−)-1,2cyclohexanediamine, compound with platinum chloride (1:1) and 1.21 g of 2,2'2''-nitrilotris-acetic acid, disilver salt in 100 ml of water was stirred overnight and then filtered. The filtrate was evaporated to dryness and the residue slurried in methanol and diluted with ether. The resulting solid was collected giving 1.4 g of the desired product.

EXAMPLE 5 cis(and trans)-1,2-Cyclohexanediamine, compound with [2-hydroxy-1,2,3-propanetricarboxylato(2-)-$O^1,O^3$]-platinum (1:1)

A 5.76 g portion of anhydrous citric acid was slurried in 40 ml of water and 6 ml of 10N sodium hydroxide was added. To the resulting solution was added a solution of 10.19 g of silver nitrate in 20 ml of water. The resulting suspension was stirred in the dark overnight and the solid collected, washed with water and dried, giving 9.7 g of citric acid, disilver salt.

A suspension of 1.14 g of 1,2-cyclohexandiamine, compound with platinum chloride (1:1), 1.22 g of citric acid, disilver salt and 100 ml of water was stirred overnight and then filtered. The filtrate was evaporated to dryness and the residue slurried in methanol and diluted with ether. The solid was collected and dried, giving 1.18 g of the desired product.

EXAMPLE 6 cis(and trans)-1,2-Cyclohexanediamine, compound with [1,2,3-propanetricarboxylato(2-)-$O^1,O^3$]platinum (1.1)

To a suspension of 2 g of cis(and trans)-1,2-cyclohexanediamine compound with platinum chloride in 20 ml of water was added a solution of 1.8 g of silver nitrate in 20 ml of water. This suspension was stirred in the dark for 3 hours and then filtered. To the filtrate was added a solution of 933 mg of 1,2,3-propanetricarboxylic acid in 5.3 ml of 2M potassium hydroxide. This mixture was stirred 1.5 hours and 390 mg of amorphous precipitate collected by filtration. The filtrate was concentrated to 10 ml and the solid collected by filtration giving an additional 1.23 g. These solids were combined, slurried in 25 ml of water and dried giving 1.03 g of the desired product.

EXAMPLE 7

1,1-Cyclobutanedimethanamine, compound with [1,1,2-ethanetricarboxylato(2-)-$O^1,O^1$]platinum (1:1)

A mixture of 20 g of 1,3-dibromopropane, 6.6 g of malononitrile and 27.6 g of potassium carbonate in 400 ml of acetonitrile was refluxed on a steam bath for 20 hours and then filtered while hot. The filtrate was concentrated to dryness, giving an oil which was taken up in methylene chloride, extracted three times with water, dried and concentrated to a dark yellow oil. This oil was vacuum distilled, giving at 41°–44° C., 0.4 mm, 6.0 g of 1,1-cyclobutanedicarbonitrile as semi-solid.

A mixture of 10.6 g of 1,1-cyclobutanedicarbonitrile and 150 ml of tetrahydrofuran was treated dropwise and rapidly with 300 ml of 1N borane in tetrahydrofuran. The reaction was cooled in an ice bath, then stirred at room temperature overnight. A 125 ml portion of ethanol was added dropwise, the reaction was stirred for 12 hours, filtered and filtrate concentrated to dryness. The residue was dissolved in 100 ml of water, basified with 6N sodium hydroxide and extracted with methylene chloride. The extract was dried, evaporated, taken up in ether and treated with 33 ml of 6N hydrochloric acid in ispropanol. The resulting solid was recrystallized from 40 ml of methanol containing 3 drops of 6N hydrochloric acid in isopropanol and 20 ml of isopropanol, giving 2.74 g of 1,1-cyclobutanedimethanamine dihydrochloride mp 240°–245° C.

A filtered solution of 1.87 g of 1,1-cyclobutanedimethanamine dihydrochloride in 30 ml of water was treated with 1.64 g of sodium acetate followed by 4.15 g of potassium tetrachloroplatinate. This mixture was filtered after one hour and the filtrate allowed to stand 24 hours and refiltered. This filtrate, after standing 24 hours, gave 430 mg of 1,1-cyclobutanedimethanamine, compound with platinum chloride (1:1) mp 280° C. dec.

A 1.35 g portion of 1,1-cyclobutanedimethanamine compound with platinum chloride was suspended in 10 ml of water and a solution of 1.02 g of silver nitrate in 10 ml of water was added. This mixture was stirred overnight, then filtered and the filtrate stirred with a solution of 486 mg of 1,1,2-ethanetricarboxylic acid in 6 ml of 1N sodium hydroxide. This mixture was allowed to stand 48 hours, the solid was collected, washed with cold water and dried, giving 800 mg of the desired product as colorless crystals, mp 228°–230° C. (dec.).

EXAMPLE 8 cis(and trans)-1,2-Cyclohexanediamine, compound with [1,1,2-ethanetricarboxylato(2-)-$O^1,O^1$]platinum (1:1)

To a solution of 2.43 g of 1,1,2-ethanetricarboxylic acid in 20 ml of water and 3 ml of 10N sodium hydroxide was added a solution of 5.09 g silver nitrate in 10 ml of water. The resulting suspension was stirred in the dark for 8 hours and the solid collected, washed with water and dried, giving 4.3 g of 1,1,2-ethanetricarboxylic acid, disilver salt.

A suspension of 1.14 g of 1,2-cyclohexanediamine, compound with platinum chloride (1:1), 1.21 g of 1,1,2-ethanetricarboxylic acid, disilver salt and 100 ml of water was stirred overnight and then filtered. The filtrate was evaporated to dryness giving 1.19 g of the desired product.

EXAMPLE 9

(1S-trans)-(−)-1,2-Cyclohexanediamine, compound with
[2-hydroxy-1,2,3-propanetricarboxylato(2-)-$O^1,O^3$]-platinum (1:1)

A solution of 1.8 g of silver nitrate in 20 ml of water was added to a suspension of 2.0 g of trans-(−)-1,2-cyclohexanediamine, compound with platinum chloride (1:1) in 20 ml of water, stirred for 3 hours and then filtered. The filtrate was evaporated to dryness and the residue slurried in a mixture of ethanol and methanol. This slurry was filtered and the filtrate evaporated to dryness. This residue was slurried in ether and the solid recovered, giving 498 mg of the desired product.

EXAMPLE 10

Diammine, compound with
[1,1,2-ethanetricarboxylato(2-)-$O^1,O^1$]platinum (1:1)

A 1.0 g portion of Cisplatin was suspended in 5 ml of water and treated with a solution of 1.14 g of silver nitrate in 5 ml of water. This mixture was stirred for 2 hours, then filtered through diatomaceous earth. The filtrate was treated with a solution of 535 mg of 1,1,2-ethanetricarboxylic acid in 6.7 ml of 1N sodium hydroxide and stirred for 2 hours. The solid was collected, washed with water and dried, giving 300 mg of the desired product, mp 229°–230° C. (dec.).

EXAMPLE 11

1,2-Diamino-1,2-dideoxy-D-glucitol, compound with
[1,1,2-ethanetricarboxylato(2-)-$O^1,O^1$]platinum (1:1)

A solution of 20 g of D-glucosamine hydrochloride in 20 ml of glacial acetic acid and 80 ml of water was heated on a steam bath for 1 hour. After cooling, the formed osazone was filtered off and discarded. The clear filtrate was reduced under 50 lb pressure in a Parr hydrogenator containing 10 ml of Raney nickel catalyst. After the reduction was complete, the catalyst was filtered off and the filtrate stirred with carbon, refiltered and extracted three times with toluene. The remaining aqueous solution was then treated with 0.68 g of sodium bicarbonate followed by a suspension of 3.32 g of potassium tetrachloroplatinate in 16 ml of water and then stirred overnight. The resulting yellow-brown solid was filtered off and recrystallized from hot water giving yellow crystals mp 262°–264° C., of 1,2-diamino-1,2-dideoxy-D-glucitol, compound with platinum dichloride (1:1).

A suspension of 1.34 g of 1,2-diamino-1,2-dideoxy-D-glucitol, compound with platinum chloride (1:1) in 10 ml of water was treated with a solution of 1.02 g of silver nitrate in 10 ml of water. After 1 hour the mixture was filtered and the filtrate treated with a solution of 1,1,2-ethanetricarboxylic acid in 6 ml of 1N sodium hydroxide. After standing 3 days the solution was filtered and the filtrate treated with one volume of isopropanol. The resulting solid was collected and dried, giving 0.64 g of the desired product, mp 195°–200° C.

EXAMPLE 12 trans-(rac.)-1,2-Cyclohexanediamine, compound with
[1-propene-1,2,3-tricarboxylato(2-)-$O^2,O^3$]platinum (1:1)

A solution of 33.2 g of potassium tetrachloroplatinate in 200 ml of water was added to a solution of 9.12 g of dl-trans-1,2-diaminocyclohexane in 40 ml of water. The suspension was stirred 3.5 hours and then the solid was collected, washed with water and dried, giving 28.8 g of trans-(rac.)-1,2-cyclohexanediamine, compound with platinum chloride (1:1).

A 3.0 g portion of trans-(rac.)-1,2-cyclohexanediamine, compound with platinum chloride (1:1) was slurried in 30 ml of water and a solution of 2.68 g of silver nitrate in 30 ml of water was added. This suspension was stirred for 3 hours, then filtered and to the filtrate was added a solution of 1.4 g of aconitic acid in 15.78 ml of 1N aqueous sodium hydroxide. This mixture was stirred in the dark for 2.5 hours, then filtered and the filtrate evaporated to dryness. The residue was slurried in a small amount of water, filtered, washed with water and dried, giving 820 mg of the

EXAMPLE 13 trans-(rac.)-1,2-Cyclohexanediamine, compound with
[2-methyl-1,2,3-propanetricarboxylato(2-)-$O^1,O^2$]-platinum (1:1)

A 3.0 g portion of trans-(rac.)-1,2-cyclohexanediamine, compound with platinum chloride was reacted as described in Example 12 producing a filtrate containing the platinum nitrate salt. To this filtrate was added a solution of 1.562 g of 96% β-methyltricarboxylic acid in 15.78 ml of 1N aqueous sodium hydroxide. To this filtrate was added a solution 1N aqueous sodium hydroxide. This mixture was stirred in the dark for 2.5 hours and further treated as described in Example 12, giving 776 mg of the desired product.

EXAMPLE 14 trans-(−)-1,2-cyclohexanediamine, compound with [2-hydroxy-1,2,3-nonadecanetricarboxylato(2-)-$O^2,O^3$]-platinum (1:1)

A solution containing trans-(−)-1,2-cyclohexanediamine, compound with potassium nitrate (prepared as described in Example 2) was treated with a suspension of agaricic acid in 30 ml of water and 4 ml of 1N sodium hydroxide. This mixture was stirred overnight and then the solid was collected, giving 1.42 g of the desired product, mp 230°–233° C. (dec.).

EXAMPLE 15

(1,1-Cyclobutanedimethananmine-N,N′)[1-propene-1,2,3-tricarboxylato(2-)-$O^2,O^3$]platinum (1:1)

A solution of 760 mg of 1,1-cyclobutanedimethanamine, compound with platinum chloride (prepared as in Example 7) and 6.68 g of silver nitrate in 50 ml of water was stirred for 2 hours and then filtered. The filtrate was treated with a solution of 348 mg of aconitic acid in 15 ml of water and 4 ml of 1N sodium hydroxide. This mixture was stirred for 48 hours, then filtered. The filtrate was concentrated to dryness and the residue triturated three times with cold water giving 100 mg of the desired product, mp 242°–244° C.

EXAMPLE 16

Trans-(1,2-Cyclohexanediamine-N-N′)[1,1,2-ethanetricarboxylato(3-)$O^1,O^1$]platinate(1-), sodium salt A 3.52 g portion of trans-(−)-1,2-cyclohexanediamine, compound with [1,1,2-ethanetricarboxylato(2-)-$O^1,O^1$]platinum (1:1) was suspended in 30 ml of water and a solution of 630 mg of sodium bicarbonate in 25 ml of water was added with stirring. The cloudy solution was filtered and the filter washed with 5 ml of water. The combined filtrate and wash was freeze-dried, giving 3.7 g of the desired product.

EXAMPLE 17

(2,2-Dimethyl-1,3-propanediamine-N,N′)[1,1,2-ethanetricarboxylato(3-)-$O^1,O^1$]platinate(1-), sodium salt A 2.058 g portion of 2,2-dimethyl-1,3-propanediamine, compound with [1,1,2-ethanetricarboxylato(2-)-$O^1,O^1$]platinum (1:1) was suspended in 5 ml of water and a solution of 378 mg of sodium bicarbonate in 10 ml of water was added. The resulting solution was filtered, degassed under a vacuum pump and freeze-dried, giving 1.92 g of the desired product.

We claim:
1. A compound of the formula:

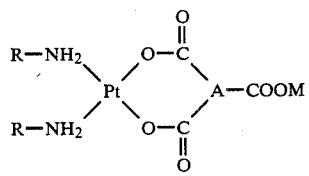

wherein M is hydrogen, sodium or potassium and R is hydrogen or alkyl($C_1$–$C_5$) or when taken together are selected from the group consisting of those of the formulae:

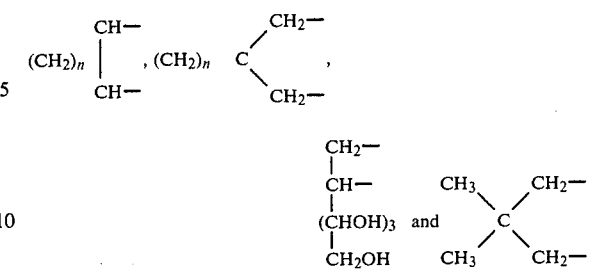

wherein n is the integer 3–5, inclusive; and A is selected from the group consisting of those of the formulae:

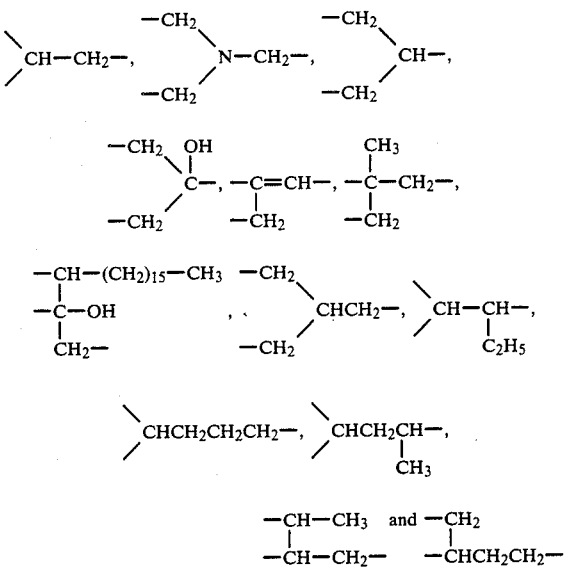

2. The compound according to claim 1, 2,2-dimethyl-1,3-propanediamine, compound with [1,1,2-ethanetricarboxylato(2-)-$O^1,O^1$]platinum (1:1).

3. The compound according to claim 1, trans-(1)-1,2-cyclohexanediamine, compound with [1,1,2-ethanetricarboxylato(2-)-$O^1,O^1$]platinum (1:1).

4. The compound according to claim 1, cis(and trans)-1,2-cyclohexanediamine, compound with [[2,2′,2″-nitrilotris[acetato]](2-)-O,$O^1$]platinum (1:1).

5. The compound according to claim 1, trans-(−)-1,2-cyclohexanediamine, compound with [[2,2′,2″-nitrilotris[acetato]](2-)-O,$O^1$]platinum (1:1).

6. The compound according to claim 1, cis(and trans)-1,2-cyclohexanediamine, compound with [2-hydroxy-1,2,3-propanetricarboxylato(2-)$O^1,O^3$]-platinum (1:1).

7. The compound according to claim 1, cis(and trans)-1,2-cyclohexanediamine, compound with [1,2,3-propanetricarboxylato(2-)-$O^1,O^3$]platinum (1:1).

8. The compound according to claim 1, 1,1-cyclobutanedimethanamine, compound with [1,1,2-ethanetricarboxylato(2-)-$O^1,O^1$]platinum (1:1).

9. The compound according to claim 1, cis(and trans)-1,2-cyclohexanediamine, compound with [1,1,2-ethanetricarboxylato(2-)-$O^1,O^1$]platinum (1:1).

10. The compound according to claim 1, (1S-trans-(−)-1,2-cyclohexanediamine, compound with [2-hydroxy-1,2,3-propanetricarboxylato(2-)-$O^1,O^3$]-platinum (1:1).

11. The compound according to claim 1, diamine compound with [1,1,2-ethanetricarboxylato(2-)-$O^1,O^1$]platinum (1:1).

12. The compound according to claim 1, 1,2-diamino-1,2-dideoxy-D-glucitol compound with [1,1,2-ethanetricarboxylato(2-)-$O^1,O^1$]platinum (1:1).

13. The compound according to claim 1, trans-(rac.)-1,2-cyclohexanediamine, compound with [1-propene-1,2,3-tricarboxylato(2-)-$O^2,O^3$]platinum (1:1).

14. The compound according to claim 1, trans-(rac.)-1,2-cyclohexanediamine, compound with [2-methyl-1,2,3-propanetricarboxylato(2-)-$O^1,O^2$]platinum (1:1).

15. The compound according to claim 1, trans-(−)-1,2-cyclohexanediamine, compound with [2-hydroxy-1,2,3-nonadecanetricarboxylato(2-)-$O^2,O^3$]platinum (1:1).

16. The compound according to claim 1, (1,1-cyclobutanedimethanamine-N,N′)-[1-propene-1,2,3-tricarboxylato(2-)-$O^2,O^3$]platinum (1:1).

17. The compound according to claim 1, trans-(1,2-cyclohexanediamine-N,N′)[1,1,2-ethanetricarboxylato(3-)$O',O'$]platinate(1-), sodium salt.

18. The compound according to claim 1, (2,2-dimethyl-1,3-propanediamine-N,N′)[1,1,2-ethanetricarboxylateo(3-)-$O',O'$]platinate(1-), sodium salt.

19. A composition of matter in dosage unit form comprising from about 1 mg to about 50 mg per square meter of body surface area of a compound of claim 1 in association with a pharmacologically acceptable carrier.

* * * * *